United States Patent [19]

Hatfield

[11] Patent Number: 4,502,988

[45] Date of Patent: Mar. 5, 1985

[54] OXIDATION PROCESS

[75] Inventor: Lowell D. Hatfield, Bargersville, Ind.

[73] Assignee: Eli Lilly and Company, Indianapolis, Ind.

[21] Appl. No.: 521,197

[22] Filed: Aug. 8, 1983

[51] Int. Cl.$^3$ ............................................. C07D 499/04
[52] U.S. Cl. .................................. 260/239.1; 544/16; 544/21; 544/30
[58] Field of Search ................. 260/239.1; 544/16, 21, 544/30

[56] References Cited

U.S. PATENT DOCUMENTS

| | | | |
|---|---|---|---|
| 3,197,466 | 7/1965 | Chow et al. | 260/239.1 |
| 3,544,581 | 12/1970 | Essery | 260/239.1 |
| 4,230,620 | 10/1980 | Chou | 260/239.1 |
| 4,287,181 | 9/1981 | Kellogg | 424/114 |

OTHER PUBLICATIONS

Wolfe et al., *Chemical Communications*, (1970) pp. 1420–1421.
Trost et al., *Tetrahedron Letters*, vol. 22, No. 14, pp. 1287–1290, 1981.
Chow et al., *J. Am. Chem. Soc.*, vol. 130, pp. 1381–1383 (1962).
Durckheimer et al., "Chapter 4 in Recent Advances in the Chemistry of α-Lactam Antibiotics," Ed. G. I. Gregory, Royal Society of Chemistry, Burlington House, London, 1980.

*Primary Examiner*—Natalie Trousop
*Assistant Examiner*—Vera C. Clarke
*Attorney, Agent, or Firm*—Charles W. Ashbrook; Arthur R. Whale

[57] ABSTRACT

Penicillin and cephalosporin sulfides and sulfoxides are readily converted to sulfones in the presence of ruthenium tetroxide.

17 Claims, No Drawings

OXIDATION PROCESS

Penicillin and cephalosporin sulfones are known generally in the art. Such compounds typically have been prepared by oxidation of the corresponding sulfides, and normally are reported only as undesirable over-oxidation products formed during the preparation of penicillin and cephalosporin sulfoxides; see "Cephalosporins and Penicillins, Chemistry and Biology" E. H. Flynn, Ed; Academic Press: New York 1972; page 138. As a result, most attempts to prepare sulfones have resulted in mixtures of sulfoxides and sulfones, with the yield of desired sulfones being somewhat low. Moreover, while many conventional oxidizing agents totally fail to give sulfones, those that do produce sulfones generally require higher reaction temperatures, which, in turn, lead to degradation of the penicillin or cephalosporin substrate.

An object of this invention is to provide a process for the preparation of penicillin and cephalosporin sulfones in high yield and high purity without resorting to high reaction temperatures.

SUMMARY OF THE INVENTION

This invention concerns a process for oxidizing penicillin and cephalosporin sulfides and sulfoxides to sulfones. The invention is more particularly directed to a process for preparing a compound of the formula

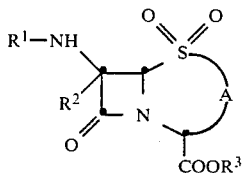

wherein:
$R^1$ is hydrogen or a carboxylic acid acyl residue;
$R^2$ is hydrogen or lower alkoxy;
$R^3$ is hydrogen, a carboxy protecting group or a salt forming group;
A is

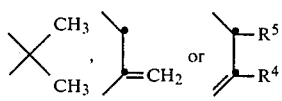

in which $R^4$ is halo, lower alkyl, lower alkoxy, or $-CH_2R^6$ where $R^6$ is lower alkanoyloxy or a heterocyclic group; and $R^5$ is hydrogen or alkoxycarbonyloxy; comprising reacting a compound of the formula

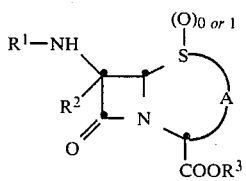

with an oxidizing agent and a catalytic amount of ruthenium tetroxide.

DETAILED DESCRIPTION OF THE INVENTION

In the above formulas, $R^1$ defines hydrogen or a carboxylic acid acyl residue. The term "carboxylic acid acyl residue" refers to any of the N-acyl side chains commonly employed in the preparation of penicillin and cephalosporin antibiotics, and typically are the acyl residues derived from $C_1$-$C_{20}$ carboxylic acids. These various carboxylic acid acyl residues are found throughout the scientific and patent literature, and no invention in the N-acyl side chain designated herein as $R^1$ is asserted or claimed in this application. Typical $R^1$ carboxylic acid acyl residues contemplated herein are those exemplified in U.S. Pat. Nos. 3,792,995, 3,883,518, 4,052,387, 3,929,775, and 3,932,393. These patents are incorporated herein by reference for their teaching of carboxylic acid acyl residues.

Preferred carboxylic acid acyl groups defined by $R^1$ include those of the formula

where $R^7$ is
(a) $C_1$-$C_7$ alkyl, cyanomethyl, $C_1$-$C_6$ haloalkyl, 4-amino-4-carboxybutyl; or
(b) $C_1$-$C_6$ alkoxy, phenoxy, benzyloxy or 4-methoxybenzyloxy; or
(c) the group $-R^8$ wherein $R^8$ is phenyl or substituted phenyl wherein the substituents are 1 or 2 halogens, hydroxy, cyano, trifluoromethyl, $C_1$-$C_4$ alkyl, $C_1$-$C_4$ alkoxy, carboxy, carboxymethyl, hydroxymethyl or aminomethyl; or
(d) an arylalkyl group of the formula $R^8$-(O)$_m$-$CH_2$- wherein $R^8$ is as defined above, and m is 0 or 1; or
(e) a substituted arylalkyl group of the formula

wherein $R^9$ is $R^8$ as defined above, 2-thienyl, 3-thienyl, 2-furyl or 3-furyl; W is hydroxy, carboxy, amino, or
(f) a heteroarylmethyl group of the formula $R^{10}$-$CH_2$- wherein $R^{10}$ is 2-thienyl, 3-thienyl, 2-furyl, 3-furyl, 2-thiazolyl, 5-tetrazolyl, 1-tetrazolyl;

$R^2$ in the above formula is hydrogen or lower alkoxy such as methoxy or ethoxy.

$R^3$ is hydrogen, a salt forming group such as sodium or potassium, or a carboxy protecting group.

In the foregoing definitions, the term "$C_1$-$C_7$ alkyl" refers to methyl, ethyl, n-propyl, n-butyl, isobutyl, pentyl, n-hexyl, isohexyl, n-heptyl and like straight and branched aliphatic hydrocarbon chains.

As used herein, "halo" includes fluoro, chloro, bromo and iodo.

The term "$C_1$-$C_6$ haloalkyl" refers to a $C_1$-$C_6$ alkyl group bearing a halo substituent. Typical haloalkyl groups include chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

In this specification, the protecting group designation generally is omitted for simplicity in nomenclature, but it is understood that, in the description of the process of this invention, each carboxy, hydroxy or amino group may be a protected group.

The term "protected amino" as employed in this application has reference to an amino group substituted with one of the commonly employed amino blocking groups such as the tert-butoxycarbonyl group (t-BOC), the benzyloxycarbonyl group, the 4-methoxybenzyloxycarbonyl group, the 2,2,2-trichloroethoxycarbonyl group, the trimethylsilyl group, and like amino protecting groups. The nature of such amino protecting groups is not critical so long as the protected amino functionality is stable under the reaction conditions described hereinafter.

The term "protected hydroxy" has reference to any group stable under the reaction conditions of the subsequent step in this synthesis of penicillin and cephalosporin sulfones, but readily cleavable thereafter. Such groups include the formyloxy group, the chloroacetoxy group, the benzhydryloxy group, the trityloxy group, the trimethylsilyl group, and the like.

The term "carboxy protecting group" or "protected carboxy" has reference to a carboxy group which has been esterified with one of the commonly used carboxylic acid protecting ester groups employed to block or protect the carboxylic acid functionality while reactions involving other functional sites of the compound are carried out. Such protected carboxy groups are noted for their ease of cleavage by hydrolytic methods to the corresponding carboxylic acid. Examples of carboxylic acid protecting groups include tert-butyl, methyl, cyanomethyl, p-methoxybenzyl, diphenylmethyl, 2,4,6-trimethylbenzyl, trityl, 4-methoxytrityl, 4,4'-dimethoxytrityl, 4,4',4"-trimethoxytrityl and like ester forming moieties. The nature of such ester forming groups is not critical so long as the ester formed therewith is stable under the reaction conditions described hereinafter. Preferred carboxylic acid protecting groups are 2,2,2-trichloroethyl, methyl, diphenylmethyl, 4-methoxybenzyl, 4-nitrobenzyl, and tert-butyl.

In the foregoing definitions, hydroxy, amino, and carboxy protecting groups are not exhaustively defined. The function of such groups is to protect the reactive functional groups during the preparation of the desired products and then to be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

When in the above definition $R^8$ represents a substituted phenyl group, $R^8$ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a cyanophenyl group, for example 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, $R^8$ represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

Illustrative of the acyl groups,

where $R^7$ is $C_1$–$C_7$ alkyl, or $C_1$–$C_6$ haloalkyl, are acetyl, propionyl, butyryl, hexanoyl, chloroacetyl, bromoacetyl and the like.

Representative of the acyl groups

when $R^7$ is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-protected aminobenzoyl.

Illustrative of the acyl groups

when $R^7$ is a group of the formula $R^8$—(O)$_m$—CH$_2$—, m is 0 and $R^8$ is phenyl or substituted phenyl, are phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when $R^7$ is a substituted arylalkyl group of the formula

are the carboxy substituted acyl groups such as the 2-carboxyl-2-phenylacetyl group of the formula

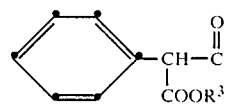

and similar groups wherein the phenyl ring is substituted, for example, 2-carboxy-2-(4-chlorophenyl)-acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-carboxymethylphenyl)acetyl, 2-carboxy-2-(4-hydroxymethylphenyl)acetyl and like groups.

Representative of the acyl groups when $R^7$ is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4-aminomethylphenyl)acetyl, 2-hydroxy-2-(3-thienyl)acetyl.

When $R^7$ is an amino substituted arylalkyl group, typical acyl groups include 2-amino-2-phenylacetyl, 2-amino-2-(4-cyanophenyl)acetyl, 2-amino-2-(4-hydroxyphenyl)acetyl, and like groups.

Representative of the acyl group

when $R^7$ is a heteroarylmethyl group of the formula $R^{10}$—$CH_2$— are 2-thienylacetyl, 3-thienylacetyl, 2-furylacetyl, 2-thiazolylacetyl, 1-tetrazolylacetyl, 5-tetrazolylacetyl and the like.

The most preferred carboxylic acid acyl residues represented by $R^1$ in the above formulas include phenylacetyl, phenoxyacetyl and 4-methylbenzoyl. It should be appreciated that the present process can be carried out on substrates having any of these side chains to provide the corresponding sulfones, which can then undergo conventional side chain cleavage and re-acylation to provide penicillin or cephalosporin sulfones bearing any desired carboxylic acid acyl residue.

$R^2$ in the above formulas defines hydrogen and lower alkoxy. The term "lower alkoxy" includes groups such as methoxy, ethoxy, n-propoxy and isobutoxy. A preferred lower alkoxy group is methoxy.

In the above formulas, when A is

the compounds defined are penicillins. When A is

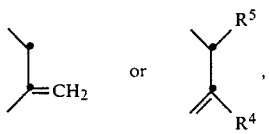

the compounds defined are cephalosporins. The oxidation process of this invention, when carried out on a substrate wherein A is

i.e. a 3-exomethylenecephalosporin sulfide or sulfoxide, effects oxidation at the sulfur atom without affecting the 3-exomethylene group. The invention accordingly offers a convenient and facile route to 3-exomethylenecepham sulfones.

$R^4$ in the above formula defines halo, such as fluoro, chloro, bromo and iodo; lower alkyl, for instance methyl or ethyl, and lower alkoxy such as methoxy, isopropoxy, n-butoxy and the like. $R^4$ additionally defines the group —$CH_2R^6$ where $R^6$ is lower alkanoyloxy or a heterocyclic group. The term "lower alkanoyloxy" means $C_1$-$C_4$ alkanoyloxy groups such as acetoxy, propionoxy and isobutyroxy. The term "heterocyclic group" includes a five or six membered heterocyclic ring containing one or more nitrogen atoms. Such groups include pyridyl, triazolyl, thiadiazolyl, tetrazoyl, and related heterocyclic groups.

According to the process of this invention, a penicillin or cephalosporin sulfide or sulfoxide is reacted with an oxidizing agent in the presence of ruthenium tetroxide to provide the corresponding penicillin or cephalosporin sulfone. The term "oxidizing agent" embraces any of the common reagents employed in the penicillin and cephalosporin arts to convert sulfides to sulfoxides. The most common oxidizing agents include peracids such as m-chloroperbenzoic acid, peracetic acid, performic acid, trifluoroperacetic acid and related peracids. Other oxidizing agents routinely employed include alkali metal metaperiodates such as sodium metaperiodate or potassium metaperiodate, and alkali metal hypohalites such as sodium hypochlorite or sodium hypobromite. If desired, ruthenium tetroxide can be employed alone as the sole oxidizing agent, however, it is preferred that this reagent be employed only in a catalytic capacity together with any of the conventional oxidizing agents.

The quantity of oxidizing agents generally employed is from about 1 to about 10 molar excess relative to the sulfide or sulfoxide substrate, more preferably about 2 to 8 molar excess. A preferred oxidizing agent according to the invention is m-chloroperbenzoic acid, and this is ideally employed in about 3 to 4 molar excess. Larger excesses of conventional oxidizing agent can be employed if desired without incurring adverse side reactions.

The process of the invention generally is carried out in a solvent, and any number of common solvents can be employed, including water. Organic solvents such as halogenated hydrocarbons (e.g., chloroform, dichloromethane), ketones (e.g. acetone, methyl ethyl ketone), and alcohols (e.g., ethanol, methanol) can be employed. If desired, the process can be carried out in a multiphase solvent system, for example in a mixture of water and a water immiscible organic solvent such as dichloromethane or chloroform.

As noted above, a preferred embodiment of this invention is the employment of ruthenium tetroxide in a catalytic amount. This amount will generally be about a 0.05 to about 0.2 molar quantity relative to the sulfide or sulfoxide substrate, and more typically about a 0.1 molar quantity. If desired, the ruthenium tetroxide can serve as the sole oxidizing agent, in which case more than a catalytic amount can be employed, for instance from about 0.1 to about a 2.0 molar quantity relative to the sulfide or sulfoxide substrate.

The ruthenium tetroxide that is employed in the oxidation process of this invention can be obtained from commercial sources and added directly to the reaction mixture, but as preferably prepared in situ by employing a catalytic amount of a lower valence ruthenium compound, such as ruthenium trichloride or ruthenium dioxide, with an oxidizing agent such as sodium metaperiodate or sodium hypochlorite. A particularly preferred method for carrying out the present process employs a catalytic amount of ruthenium trichloride and an excess of aqueous sodium hypochlorite. This method of preparing ruthenium tetroxide is described in detail by Wolfe et al., *Chemical Communications*, 1420 (1970). Other lower valence ruthenium compounds that can be employed in the generation of ruthenium tetroxide include ruthenium tribromide, ruthenium dioxide and related ruthenium compounds. All that is required according to the present invention is that ruthenium tetroxide be present in the reaction mixture.

The oxidation process of this invention is generally carried out at a temperature of about $-20°$ to about $50°$ C., and preferably at about $0°$ to about $20°$ C. The reaction is substantially complete within about 1 to about 24 hours, although longer reaction times are not detrimental and can be employed if desired.

The sulfone that is prepared according to the present process can be isolated by conventional techniques. If desired, an agent such as trimethyl phosphite can be added to the reaction mixture in order to quench the reaction, and then the product can be recovered by filtration or by removal of the solvent from the reaction mixture, for example by evaporation under reduced pressure or the like. The product sulfone can be purified further if needed by standard methods such as chromatography, crystallization, and the like.

As already pointed out, the penicillin and cephalosporin sulfones prepared according to the process of this invention are known in the art. Penicillin sulfones have found widespread use as $\beta$-lactamase inhibitors, for example as described by Kellogg in U.S. Pat. No. 4,287,181. The cephalosporin sulfones are of particular importance as intermediates, especially in the synthesis of new antibiotics such as 1-oxacephems and the like, and also have been reported to exhibit antibacterial activities.

Specific aspects of the present process are illustrated in the following working examples. The examples are not intended to limit any aspect of the invention and should not be so construed.

EXAMPLE 1 p-Nitrobenzyl 7-phenoxyacetamido-1,1-dioxo-3-exomethylenecepham-4-carboxylate

To a stirred solution of 2.5 g (5 mM) of p-nitrobenzyl 7-phenoxyacetamido-1-oxo-3-exomethylenecepham-4-carboxylate in 25 ml of dichloromethane were added 10 ml of water and 0.25 ml of a 2% aqueous solution of ruthenium trichloride. To the stirred reaction solution were added 50 ml of sodium hypochlorite in about 2.5 ml portions over a 20 minute period. The reaction mixture was stirred for 30 minutes at room temperature following complete addition of the sodium hypochlorite. The organic layer was then separated and washed three times with 50 ml portions of 10% aqueous sodium chloride solution. After drying the organic layer, the solvent was removed by evaporation under reduced pressure to provide 2.2 g of a white foam. Crystallization of the product from 50 ml of hot methanol afforded 1.5 g of white crystals identified as p-nitrobenzyl 7-phenoxyacetamido-1,1-dioxo-3-exomethylenecepham-4-carboxylate.

NMR (CDCl$_3$) $\delta$3.9 (s, 2H); $\delta$5.2 (d, 1H); $\delta$5.3 (s, 2H); $\delta$5.5 (d, 2H); $\delta$6.1 (dd, 1H); $\delta$6.7–7.3 (m, 5H); $\delta$7.5 (d, 2H); $\delta$8.2 (d, 2H).

EXAMPLE 2

7-(4-methylphenyl)formamido-1,1-dioxo-3-methyl-3-cephem-4-carboxylic acid

A suspension of 1.0 g of 7-(4-methylphenyl)-formamido-3-methyl-3-cephem-4-carboxylic acid in 10 ml of water was stirred and the pH was adjusted to 7.0 by the addition of about 4 ml of 20% aqueous trisodium phosphate. The reaction mixture was stirred at room temperature while approximately 20 mg of ruthenium trichloride as the trihydrate were added, followed by the addition of 1.5 g of sodium metaperiodate. The pH of the reaction mixture was maintained at about 6.5 by the addition of 20% aqueous trisodium phosphate as needed. After stirring the reaction mixture for about 1 hour, a thin-layer chromatographic anaylsis indicated a small amount of starting material remaining in the reaction mixture. An additional 0.3 g of sodium metaperiodate was then added to the mixture and the solution was stirred for an additional one-half hour. The reaction mixture was then diluted by the addition of about 20 ml of water and the pH of the mixture was adjusted to 2.2 by the slow addition of 15% aqueous sulfuric acid. The precipitated solid which formed was collected by filtration and air dried at room temperature in a vacuum for 16 hours, and then for 1 hour at 40° C. The product thus obtained weighed 0.08 g for a yield of 69%. Recrystallization of 0.2 g of the product in 10 ml of acetone, 5 ml of methanol, and 5 ml of isopropyl alcohol afforded 0.17 g of 7-(4-methylphenyl)-formamido-1,1-dioxo-3-methyl-3-cephem-4-carboxylate acid. M.P. 201°–202° C. (dec).

Analysis calculated for $C_{16}H_{16}N_2O_6S$. Theory: C, 52.74; H, 4.43; N, 7.69; O, 26.34, S, 8.80; Found: C, 52.47; H, 4.70; N, 7.49; O, 26.62 S, 8.78. NMR (DMSOd$_6$): $\delta$2.0 (s, 3H, CH$_3$); $\delta$2.3 (s, 3H, CH$_3$); $\delta$4.2 (s, 2H, C$^2$ methylene); $\delta$5.28 (doublet, 1H, C$^6$); $\delta$6.02 (dd, 1H, C$^7$); $\delta$7.5 (dd, 4H, aromatic); $\delta$8.6 (d, 1H, NH) IR (mull) 1335 cm$^{-1}$ sulfone.

EXAMPLE 3

7-(4-methylphenyl)formamido-1,1-dioxo-3-methyl-3-cephem-4-carboxylic acid

A suspension of 20.0 g (60 mM) of 7-(4-methylphenyl)formamido-3-methyl-3-cephem-4-carboxylic acid in 200 ml of water was stirred at room temperature while a solution of 20% aqueous trisodium phosphate was added dropwise until the pH was 7.0. The reaction mixture was then cooled to about 5° C. in an ice-water bath and stirred while 0.2 g of ruthenium trichloride trihydrate were added in one portion. With continued stirring, 36 g of sodium metaperiodate powder were added to the reaction mixture portion-wise while maintaining the temperature at about 5°–10° C. and the pH at about 6.0 to 7.0 by addition of 20% aqueous trisodium phosphate as needed. Following complete addition of the sodium metaperiodate, the reaction mixture was stirred for 30 minutes and then the pH was adjusted to 2.0 by the addition of about 20 ml of 15% aqueous sulfuric acid. The precipitated product was removed by filtration and washed with water. The product was dissolved in about 1500 ml of 2:1 acetone-methanol (v/v). This solution was stirred and diluted with 200 ml of isopropanol, dried and then filtered. The resulting solution was cooled to about 15° C. for 12 hours and then the solvent was removed under reduced pressure to a volume of approximately 200 ml. The solution was diluted by the addition of 200 ml of water and stirred for 30 minutes and then filtered. The precipitate was washed with 150 ml of a one-to-one mixture of isopropanol and water and then dried in a vacuum at 40° C. to provide 14.91 g of a beige-colored solid. Yield 68.0%. This product was identified as 7-(4-methylphenyl)formamido-1,1-dioxo-3-methyl-3-cephem-4-carboxylic acid. M.P. 203°–204° C. (dec). The NMR when run in DMSOd$_6$ was consistent with that obtained for the product prepared as described in Example 2.

EXAMPLE 4

Sodium 7-(4-methylphenyl)formamido-1,1-dioxo-3-methyl-3-cephem-4-carboxylate

A suspension of 1.0 g (3 mM) of 7-(4-methylphenyl)formamido-3-methyl-3-cephem-4-carboxylic acid in 10 ml of water was stirred at room temperature and the pH of the suspension was adjusted to 8.0 by the dropwise addition of 50% aqueous tripotassium phosphate. The reaction mixture was cooled to 10° C. and stirred while about 20 mg of ruthenium trichloride trihydrate were added in one portion. To the cold stirred reaction mixture were added dropwise over 30 minutes 50 ml of 5% aqueous sodium hypochlorite solution. The reaction mixture was stirred at 10° C. for 1 hour following complete addition of the sodium hypochlorite, and then was warmed to room temperature and allowed to stir for 12 hours. The pH of the reaction mixture was adjusted to 7.2 by the addition of 5% hydrochloric acid. The reaction mixture was stored for 16 hours at −10° C. and then filtered. The solid filter cake was washed with 10 ml of 5% aqueous sodium chloride solution. The filter cake was then dissolved in 10 ml of methanol and this alcoholic solution was filtered through high-flow supercell to remove any remaining ruthenium salts. The filtrate was concentrated to a volume of about 5 ml by evaporation under reduced pressure. A white crystalline solid which formed was collected by filtration and dried to provide 0.63 g of sodium 7-(4-methylphenyl)formamido-1,1-dioxo-3-methyl-3-cephem-4-carboxylate. M.P. 190°–192° C. (dec). NMR was consistent with the structure proposed for the desired sulfone. IR (KBr) 1330 cm$^{-1}$ sulfone.

EXAMPLE 5 p-Nitrobenzyl 7-phenoxyacetamido-1,1-dioxo-3-exomethylenecepham-4-carboxylate

Ruthenium tetroxide was prepared by reacting 26 mg (0.1 mM) of ruthenium trichloride trihydrate in 25 ml of acetone with 0.5 mM of meta-chloroperbenzoic acid for 10 minutes at 10° C. under a nitrogen atmosphere. This reaction mixture was stirred at 10° C. while 4.99 g (10 mM) of p-nitrobenzyl 7-phenoxyacetamido-3-exomethylenecepham-4-carboxylate were added in one portion. The reaction mixture was stirred while 8.0 g (40 mM) of m-chloroperbenzoic acid in 40 ml of acetone were added dropwise over a 10 minute period. The reaction mixture was warmed to room temperature following complete addition of the m-chloroperbenzoic acid, and stirring was continued for 2 hours. The reaction was terminated by the addition of 3 ml of trimethyl phosphate. The solvent was then removed from the reaction mixture by evaporation under reduced pressure. The residue was dissolved in ethyl acetate and washed with aqueous sodium carbonate in brine. The organic layer was dried and the solvent was removed by evaporation under reduced pressure to provide an oil. The oil was crystallized from 50 ml of methanol to afford 4.67 g of p-nitrobenzyl 7-phenoxyacetamido-1,1-dioxo-3-exomethylenecepham-4-carboxylate. Yield 90.7%.

Analysis calculated for C$_{23}$H$_{21}$N$_3$O$_9$S. Theory: C, 53.59; H, 4.11; N, 8.15; S, 6.22; Found: C, 53.49; H, 4.05; N, 8.02; S, 6.22.

NMR (DMSOd$_6$): δ3.41 (s, 2H, C$^2$); δ4.35 (s, 2H, =CH$_2$); δ4.72 (s, 2H, OCH$_2$—); δ5.33 (s, 1H, C$^4$); δ5.4 (s, 2H, CO$_2$CH$_2$—); δ5.68 (d, 1H, C$^6$); δ5.78 (s, δ6.15 (dd, 1H, C$^7$); δ6.9–8.8 (m, 0H, aromatic). IR (CHCL$_3$) 1360 cm$^{-1}$ sulfone.

EXAMPLE 6 p-Nitrobenzyl 6-phenylacetamido-1,1-dioxo-penam-3-carboxylate

To a cold (10° C.) stirred solution of 4.86 g (10 mM) of p-nitrobenzyl 6-phenylacetamido-penam-4-carboxylate in 25 ml of acetone containing 0.026 g (0.1 mM) of ruthenium trichloride trihydrate and 0.085 g (0.5 mM) of meta-chloroperbenzoic acid was stirred at 10° C. for 20 minutes under a nitrogen atmosphere. A solution of 8.0 g of meta-chloroperbenzoic acid in 40 ml of acetone was added dropwise to the reaction mixture over 30 minutes. Following complete addition, the reaction mixture was stirred at about −10° C. for 1 hour. Thin-layer chromatographic analysis indicated the reaction mixture contained a small amount of sulfide starting material. An additional 1.72 g of meta-chloroperbenzoic acid were added to the reaction mixture in one portion and stirring was continued at 0° to −10° C. for 30 minutes. Thin-layer chromatographic analysis indicated a small amount of sulfide was still present in that reaction mixture. An additional 1.72 g of meta-chloroperbenzoic acid were added to the mixture and stirring was continued for an additional 30 minutes at 0° to −10° C., at which time thin-layer chromatographic analysis indicated that the reaction was complete. The reaction was quenched by the addition of trimethylphosphite and the solvent was removed by evaporation under reduced pressure to provide an oily residue. The residue was dissolved in ethyl acetate and washed with dilute sodium carbonate and brine. After drying the organic solution, the solvent was removed by evaporation under reduced pressure to provide the product as an oil. Crystallization of the oil from 50 ml of methanol afforded 2.56 g of p-nitrobenzyl 6-phenylacetamido-1,1-dioxo-penam-4-carboxylate. Yield 49.5%.

Analysis calculated for C$_{23}$H$_{23}$N$_3$O$_8$S. Theory: C, 55.08; H, 4.62; N, 8.38; S, 6.39; O, 25.52; Found: C, 54.90; H, 4.75; N, 8.59; S, 6.41; O, 25.32.

NMR (DMSOd$_6$): δ1.14 (s, 3H, CH$_3$); δ1.6 (s, 3H, CH$_3$); δ3.63 (s, 2H, CH$_2$CO); δ4.61 (s, 1H, C$^3$); δ5.41 (s, 2H, COOCH$_2$); δ5.43 (s, 1H, C$^5$); δ5.82 (dd, 1H, C$^6$); δ7.36 (s, 5H, phenyl); δ7.63-δ-8.45 (m, 5H, aromatic and NH). IR (CHCl$_3$) 1360 cm$^{-1}$ sulfone.

EXAMPLE 7

2,2,2-Trichloroethyl 7-phenoxyacetamido-1,1-dioxo-3-methyl-3-cephem-4-carboxylate A solution of 0.026 g (0.1 mM) of ruthenium trichloride trihydrate in 25 ml of acetone containing 0.5 mM of m-chloroperbenzoic acid was stirred for 10 minutes at 0° to −10° C. under a nitrogen atmosphere. To the stirred reaction mixture were added 4.94 g (10 mM) of 2,2,2-trichloroethyl 7-phenoxyacetamido-1-oxo-3-methyl-3-cephem-4-carboxylate in one portion, followed by the portion-wise addition over ten minutes of a solution of 8.0 g (40 mM) of m-chloroperbenzoic acid in 40 ml of acetone. Following the complete addition, the reaction mixture was warmed to room temperature and stirred for 4 hours. Thin-layer chromatographic analysis indicated that no starting material remained in the reaction mixture. Trimethylphosphite was added to the reaction mixture until a negative starch iodide test was obtained. The solvent was removed from the reaction mixture by evaporation under reduced pressure to provide a solid. The solid was dissolved in 100 ml of ethyl acetate and washed twice with 100 ml portions of dilute sodium carbonate and then with water and finally with brine. The solution was dried and the solvent was removed by evaporation under reduced pressure to provide an oil. Crystallization of the oil from 50 ml of methanol afforded 2.91 g of 2,2,2-trichloroethyl 7-phenoxyacetamido-1,1-dioxo-3-methyl-3-cephem-4-carboxylate. Yield 57%.

Analysis calculated for $C_{18}H_{17}N_2O_7SCl_3$. Theory: C, 42.25; H, 3.35; N, 5.47; S, 6.27; O, 21.88; Cl, 20.78; Found: C, 41.96; H, 3.53; N, 4.68; S, 6.09; O, 21.66; Cl, 20.74.

NMR (DMSOd$_6$): $\delta$2.12 (s, 3H, CH$_3$); $\delta$3.38 (s, 2H, C$^2$); $\delta$4.41 (s, 2H, CH$_2$CO); $\delta$5.18 (s, 2H, CO$_2$CH$_2$); $\delta$5.41 (d, 1H, C$^6$); $\delta$6.18 (dd, 1H, C$^7$); $\delta$6.85–7.6 (m, 6H, aromatic and NH). IR (KBr) 1335 cm$^{-1}$ sulfone.

EXAMPLE 8

7-(4-Methylphenyl)formamido-1,1-dioxo-3-acetoxymethyl-3-cephem-4-carboxylic acid To a stirred solution of 0.026 g (0.1 mM) of ruthenium trichloride trihydrate in 25 ml of acetone containing 0.5 mM of m-chloroperbenzoic acid were added in one portion 3.76 g (10 mM) of 7-(4-methylphenyl)formamido-3-acetoxymethyl-3-cephem-4-carboxylic acid. The reaction mixture was stirred while 8.0 g (40 mM) of m-chloroperbenzoic acid in 40 ml of acetone was added dropwise over 10 minutes. Following complete addition, the reaction mixture was warmed to room temperature and stirred for 4 hours. Thin-layer chromatographic analysis demonstrated the product to be the desired sulfone with a small amount of sulfoxide. The reaction was quenched by the addition of trimethylphosphite until a negative starch iodide test was obtained. The solvent was removed from the reaction mixture by evaporation under reduced pressure to provide a solid. The solid was dissolved in ethyl acetate and washed with aqueous sodium carbonate in brine, dried, and the solvent was removed by evaporation to provide a solid. Following crystallization of the solid from 50 ml of methanol there was obtained 1.42 g of 7-(4-methylphenyl)formamido-1,1-dioxo-3-acetoxymethyl-3-cephem-4-carboxylic acid. Yield 34.8%.

Analysis calculated for $C_{18}H_{18}N_2O_8S$. Theory: C, 51.18; H, 4.30; N, 6.63; S, 7.59 O, 30.30; Found: C, 51.49; H, 4.17; N, 6.38; S, 7.39 O, 30.14.

NMR (DMSOd$_6$): $\delta$2.03 (s, 3H, CH$_3$); $\delta$2.38 (s, 3H, COCH$_3$); $\delta$3.38 (s, 2H, C$^2$); $\delta$4.32 (s, 2H, CH$_2$OCO); $\delta$5.45 (d, 1H, C$^6$); $\delta$6.2 (dd, 1H, C$^7$); $\delta$7.25–8.0 (q, 1H, aromatic); $\delta$8.3 (d, 1H, NH); IR (CHCl$_3$) 1345 cm$^{-1}$ sulfone.

EXAMPLE 9

Methyl 6-phenylacetamido-1,1-dioxo-penam-3-carboxylate

To a solution of 34.36 g (94.27 mM) of methyl 6-phenylacetamido-1-oxo-penam-3-carboxylate in 250 ml of dichloromethane was added dropwise a solution of 0.05 g of ruthenium dioxide and 26.17 g (122.8 mM) of sodium periodate in 400 ml of water. The reaction mixture was stirred at room temperature for 90 minutes. The organic layer was then separated and dried and the solvent was removed by evaporation under reduced pressure to a volume of about 75 ml. This solution was passed over a column packed with 40 g of silica gel, eluting with ethyl acetate. The appropriate fractions were combined and the solvent was removed by evaporation under reduced pressure to provide a product that, when crystallized from dichloromethane and diethyl either, was identified as 24 g of methyl 6-phenylacetamido-1,1-dioxo-penam-3-carboxylate.

Elemental analysis calculated for $C_{17}H_{20}N_2O_6S$. Theory: C, 53.67; H, 5.30; O, 25.23; N, 7.36; Found: C, 53.56; H, 5.07; O, 25.38; N, 7.17.

NMR (CDCl$_3$) $\delta$1.2 (s, 3H, CH$_3$); $\delta$1.5 (s, 3H, CH$_3$); $\delta$3.5 (s, 2H, CH$_2$CO); $\delta$3.7 (s, 3H, COOCH$_3$); $\delta$4.4 (s, 1H, C$^3$); $\delta$4.7 (d, 1H, C$^5$); $\delta$6.0 (dd, 1H, C$^6$); $\delta$6.9 (d, 1H, NH); $\delta$7.2 (m, 5H, aromatic). IR (KBr) 1330 cm$^{-1}$ sulfone.

EXAMPLE 10

2,2,2-Trichloroethyl 7-phenoxyacetamido-1,1-dioxo-2$\beta$-methoxycarbonyloxy-3-methyl-3-cephem-4-carboxylate To a stirred solution of 2.2 g of 2,2,2-trichloroethyl 7-phenoxyacetamido-2$\beta$-methoxycarbonyloxy-3-methyl-3-cephem-4-carboxylate in 80 ml of dichloromethane was added a suspension of 4.31 g (20.15 mM) of sodium periodate and 0.05 g of ruthenium dioxide in 80 ml of water containing one normal sodium hydroxide to pH 6.6. The two-phase reaction mixture was stirred at room temperature for 20 hours and then the organic phase was separated and the aqueous phase was washed with fresh dichloromethane. The organic layers were combined, dried, and concentrated to a volume of about 30 ml by evaporation under reduced pressure. The concentrated solution was filtered through silica gel and the solvent was removed from the filtrate by evaporation under reduced pressure. The product thus formed was crystallized from isopropyl ether and dichloromethane to give 0.81 g of 2,2,2-trichloroethyl 7-phenoxyacetamido-1,1-dioxo-2$\beta$-methoxycarbonyloxy-3-methyl-3-cephem-4-carboxylate.

Analysis calculated for $C_{20}H_{19}N_2O_{10}S_1Cl_3$. Theory: C, 41.01; H, 3.26; N, 4.78; O, 27.31; Found: C, 40.82; H, 3.11; N, 4.62; O, 27.22.

NMR (CDCl$_3$) $\delta$2.18 (s, 3H, CH$_3$); $\delta$3.92 (s, 3H CH$_3$); $\delta$4.5 (s, 2H CH$_2$CCl$_3$); $\delta$4.96 (q, 2H, CH$_2$); $\delta$5.0 (d, 1H, C$^6$); $\delta$5.67 (s, 1H, C$^2$); $\delta$6.3 (dd, 1H, C$^7$); $\delta$6.8–7.4 (m, 5H, aromatic); $\delta$7.9 (d, 1H, NH). IR (KBr) 1358 cm$^{-1}$ sulfone.

EXAMPLE 11

6-Phenoxyacetamdio-1,1-dioxo-penam-3-carboxylic acid

To a stirred solution of 25 g (68 mM) of 6-phenoxyacetamido-1-oxo-penam-3-carboxylic acid in 300 ml of 30% water/acetone (v/v) were added portionwise over 10 minutes 44.0 g (205 mM) of sodium periodate. Once all of the sodium periodate had dissolved, the reaction mixture was cooled to 0° C. and stirred at that temperature while 0.09 g (0.68 mM) of ruthenium dioxide was added in one portion. The reaction mixture was then warmed to room temperature and stirred for 45 minutes.

The acetone was removed from the reaction mixture by evaporation under reduced pressure. The product was isolated from the aqueous mixture by extraction with chloroform. The chloroform extracts were combined, washed with fresh water, dried, and the solvent was removed by evaporation to give 19.5 g of 6-phenoxyacetamido-1,1-dioxo-penam-3-carboxylic acid. Yield 75%.

NMR (CDCl$_3$+acetone d$_6$): δ1.45 (s, 3H, CH$_3$); δ1.6 (s, 3H, CH$_3$): δ4.6 (s, 2H, CH$_2$CO); δ4.99 (d, 1H, C$^5$); δ6.21 (dd, 1H, C$^6$); δ6.8–7.5 (m, 5H, aromatic); δ8.22 (d, 1H, NH); δ10.2 (s, 1H, COOH).

EXAMPLE 12

As noted above, many of the cephalosporin sulfones prepared by the process of this invention are useful in the synthesis of 1-oxadethiacephalosporin antibiotics. Of particular importance as intermediates are the 3-exomethylene sulfones. Reaction of these compounds with a metal such as zinc and a protonic acid provides azetidinone sulfinic acids. The sulfinic acids are converted to 4-halozetidinones by reaction with a halogenating agent such as N-chlorosuccinimide. The haloazetidinones are converted to 1-oxadethiacephalosporins by the methods described in U.S. Pat. Nos. 4,013,653 and 4,234,724.

By following the general procedures of Examples 1–11, diphenylmethyl 7-β-(4-methylphenylcarboxamido)-3-exomethylenecepham-4-carboxylate can be oxidized to the sulfone. Conversion of the sulfone to a sulfinic acid can be accomplished as follows:

A suspension of 3.18 g (6 mM) of diphenylmethyl-7-β-(4-methylphenylcarboxamido)-3-exomethylenecepham-1,1-dioxide-4-carboxylate in 35 ml of N,N-dimethylformamide and 5 ml of water was stirred at 25° C. under a nitrogen blanket. Six grams of ammonium chloride were added in one portion to the reaction mixture, followed by the addition of 7.5 g of zinc metal dust that had been washed with 50 ml of 1N hydrochloric acid. The reaction mixture was stirred for twenty-four hours at 25° C., and then filtered through hyflo filter aid. The filter cake was washed with 20 ml of N,N-dimethylformamide and then with 200 ml of ethyl acetate. The filtrate was washed three times with 100 ml portions of 5% (v/v) aqueous hydrochloric acid. The organic layer was separated, washed with brine, dried, and the solvent was removed by evaporation under reduced pressure to give 3.5 g of a white foam identified as diphenylmethyl-3-methyl-2-(2-sulfinyl-4-oxo-3-(4-methylbenzoylamino)-1-azetidinyl)-2-butenoate. IR(CHCl$_3$): 1778 cm$^{-1}$.

NMR (CDCl$_3$): δ2.01–2.25 (three singlets, 3H each); δ4.70 (d, 1H); δ5.60 (dd, 1H); δ6.1–7.9 (m, 15H); δ9.35 (s, 1H).

I claim:

1. A process for preparing a penicillin or cephalosporin sulfone of the formula

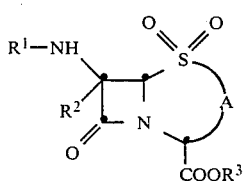

wherein:
R$^1$ is hydrogen or a carboxylic acid acyl residue;
R$^2$ is hydrogen or lower alkoxy;
R$^3$ is hydrogen, a carboxy protecting group or a salt forming group;
A is

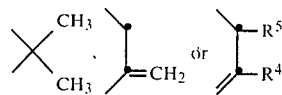

in which:
R$^4$ is halo, lower alkyl, lower alkoxy, or —CH$_2$R$^6$, wherein R$^6$ is lower alkanoyloxy or a heterocyclic group; and
R$^5$ is hydrogen or alkoxycarbonyloxy; comprising reacting a compound of the formula

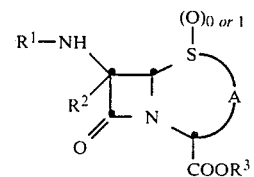

with about 1 to about 10 molar excess of an oxidizing agent and a catalytic amount of ruthenium tetroxide in a suitable solvent at a temperature of about −20° C. to about 50° C.

2. The process of claim 1 wherein R$^1$ is a carboxylic acid acyl residue of the formula

where R$^7$ is:
(a) C$_1$–C$_7$ alkyl, cyanomethyl, C$_1$–C$_6$ haloalkyl, 4-amino-4-carboxybutyl; or
(b) C$_1$–C$_6$ alkoxy, phenoxy, benzyloxy or 4-methoxybenzyloxy; or
(c) the group —R$^8$ wherein R$^8$ is phenyl or substituted phenyl wherein the substituents are 1 or 2 halogens, hydroxy, cyano, trifluoromethyl, C$_1$–C$_4$ alkyl, C$_1$–C$_4$ alkoxy, carboxy, carboxymethyl, hydroxymethyl or aminomethyl; or
(d) an arylalkyl group of the formula R$^8$—(O)$_m$—CH$_2$— wherein R$^8$ is as defined above, and m is 0 or 1; or
(e) a substituted arylalkyl group of the formula

wherein R$^9$ is R$^8$ as defined above, 2-thienyl, 3-thienyl, 2-furyl or 3-furyl; W is hydroxy, carboxy, amino, or
(f) a heteroarylmethyl group of the formula R$^{10}$—CH$_2$— wherein R$^{10}$ is 2-thienyl, 3-thienyl, 2-furyl, 3-furyl, 2-thiazolyl, 5-tetrazolyl, 1-tetrazolyl;
R$^2$ in the above formula is hydrogen or lower alkoxy such as methoxy or ethoxy;
R$^3$ is hydrogen, a salt forming group, or a carboxy protecting group.

3. The process of claim 2 where $R^3$ is hyrogen, sodium, potassium, 2,2,2-trichloroethyl, 4-nitrobenzyl, methyl or diphenylmethyl.

4. The process of claim 3 where $R^2$ is hydrogen.

5. The process of claim 4 wherein A is

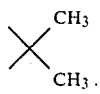

6. The process of claim 5 wherein $R^1$ is phenoxyacetyl, 4-methylbenzoyl, or phenylacetyl.

7. The process of claim 4 where A is

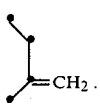

8. The process of claim 7 wherein $R^1$ is phenoxyacetyl, 4-methylbenzoyl or phenylacetyl.

9. The process of claim 4 wherein A is

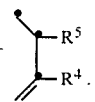

10. The process of claim 9 wherein $R^5$ is hydrogen.

11. The process of claim 10 wherein $R^4$ is methyl.

12. The process of claim 10 wherein $R^4$ is acetoxymethyl.

13. The process of claim 9 wherein $R^5$ is

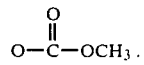

14. The process of claim 1 wherein the ruthenium tetroxide is formed in situ.

15. The process of claim 1 wherein the oxidizing agent exployed is m-chloroperbenzoic acid.

16. The process of claim 1 wherein the oxidizing agent employed is sodium metaperiodate.

17. The process of claim 1 wherein the oxidizing agent employed is sodium hypochlorite.

* * * * *